US009486610B2

(12) United States Patent
Slavin (10) Patent No.: US 9,486,610 B2
(45) Date of Patent: Nov. 8, 2016

(54) IMPLANTER DEVICE FOR NERVE STIMULATION AND METHOD OF USING THE SAME

(71) Applicant: Konstantin V. Slavin, Oak Park, IL (US)

(72) Inventor: Konstantin V. Slavin, Oak Park, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 13/886,808

(22) Filed: May 3, 2013

(65) Prior Publication Data

US 2013/0296989 A1    Nov. 7, 2013

Related U.S. Application Data

(60) Provisional application No. 61/642,138, filed on May 3, 2012.

(51) Int. Cl.
| | |
|---|---|
| *A61M 5/32* | (2006.01) |
| *A61M 25/00* | (2006.01) |
| *A61N 1/05* | (2006.01) |
| *A61B 17/34* | (2006.01) |

(52) U.S. Cl.
CPC ...... *A61M 25/0084* (2013.01); *A61B 17/3468* (2013.01); *A61N 1/0551* (2013.01); *A61N 1/05* (2013.01)

(58) Field of Classification Search
CPC .... A61N 5/1007; A61N 1/0551; A61N 1/05; A61B 17/3403; A61B 2017/3407; A61B 17/3468; A61M 25/0084
USPC ....... 607/116, 117; 604/272, 164.01, 170.02, 604/170.03
See application file for complete search history.

(56) References Cited

U.S. PATENT DOCUMENTS

| | | | | |
|---|---|---|---|---|
| 5,628,734 | A | * | 5/1997 | Hatfalvi ............. A61B 17/3401 604/158 |
| 2003/0036787 | A1 | * | 2/2003 | Redko .................. A61N 1/0553 607/117 |
| 2007/0021767 | A1 | * | 1/2007 | Breznock ......... A61B 17/00234 606/185 |

* cited by examiner

*Primary Examiner* — Edward Moran
*Assistant Examiner* — Michael Carey
(74) *Attorney, Agent, or Firm* — Michael Best & Friedrich LLP (57) ABSTRACT

The present invention is directed to an implanter for nerve stimulation. The implanter comprises a plurality of preformed stylets and a hollow needle. Each preformed stylet defines a butt end, a tip opposite the butt end, and a curved portion extending therebetween. The needle defines a first end configured to receive each preformed stylet, a second end opposite the first end, and a curved portion extending therebetween. The curved portion of the needle and the curved portion of the preformed stylets are of substantially congruent shapes such that the preformed stylets are interchangeably insertable into the needle.

11 Claims, 9 Drawing Sheets

IMPLANTER DEVICE FOR NERVE STIMULATION AND METHOD OF USING THE SAME

CROSS-REFERENCE TO RELATED APPLICATIONS

This application claims the benefit of priority to U.S. Provisional Patent Application No. 61/642,138, filed May 3, 2012, the content of which is incorporated herein by reference in its entirety.

FIELD OF THE INVENTION

The present disclosure relates to the development and use of an implanter for nerve stimulation.

BACKGROUND OF THE INVENTION

Electrical stimulation of peripheral nerves is used in a variety of medical applications. For example, such uses include testing neuromuscular conduction in anesthesia and intensive care units, motor stimulation of phrenic nerves in cases of diaphragmal palsy and somatic nerves of the extremities in patients with hemiplegia and paraplegia, vagal nerve stimulation for treatment of intractable epilepsy and refractory depression, autonomic stimulation for urinary and gastrointestinal disorders, carotid sinus stimulation for hypertension and angina pectoris, and the stimulation of peripheral nerves for control of neuropathic pain. In general, an electrical energy is delivered to the peripheral nerve by small metal contacts that are arranged on a lead or electrode.

Peripheral nerve stimulation is typically performed with devices designed and developed for the percutaneous insertion of spinal cord stimulation electrodes. For example, straight linear stylets that facilitate electrode lead advancement in the epidural space may be used for spinal cord stimulation applications with guidewires and straight linear needles or introducers. However, removing the stylet and advancing an implant for peripheral nerve stimulation using such devices can be difficult or cumbersome, because the straight linear shapes of the stylet and needle may not conform to the natural body curvature when used for peripheral nerve stimulation. Thus, there has developed a need for a tool that can allow for an easy introduction of an implant for peripheral nerve stimulation.

SUMMARY OF THE INVENTION

The present disclosure is directed to an implanter for nerve stimulation, the implanter comprising a plurality of preformed stylets and a hollow needle. Each preformed stylet defines a butt end, a tip opposite the butt end, and a curved portion extending therebetween. The needle defines a first end configured to receive each preformed stylet, a second end opposite the first end, and a curved portion extending therebetween. The curved portion of the needle and the curved portion of the preformed stylets are of substantially congruent shapes such that the preformed stylets are interchangeably insertable into the needle.

The invention is also directed to a method of introducing an implant for stimulating a nerve. A hollow needle carrying a preformed stylet is inserted into a target region. The preformed stylet defines a butt end, a tip opposite the butt end, and a curved portion extending therebetween. The needle defines a first end configured to receive the preformed stylet, a second end opposite the first end, and a curved portion extending therebetween. The curved portion of the needle and the curved portion of the preformed stylets are of substantially congruent shapes. The preformed stylet is withdrawn to leave the needle in place in the target region. The implant is inserted into the needle. The needle is removed from the target region to expose the implant therein.

Other aspects of the invention will become apparent by consideration of the detailed description and accompanying drawings.

DETAILED DESCRIPTION

Described herein is an implanter including a plurality of preformed stylets and a hollow needle to facilitate insertion of implant(s) for peripheral nerve stimulation or subcutaneous neurostimulation. The preformed stylets and hollow needle each include curved portions to conform to the natural curvature of the human body and to advance an implant to a position away from the skin surface. The curved portions of the preformed stylets and hollow needle are of substantially congruent shapes such that the preformed stylets are interchangeably insertable into the hollow needle.

1. Definitions

The terminology used herein is for the purpose of describing particular embodiments only and is not intended to be limiting. As used in the specification and the appended claims, the singular forms "a," "and," and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

2. Implanter

Figure 1:
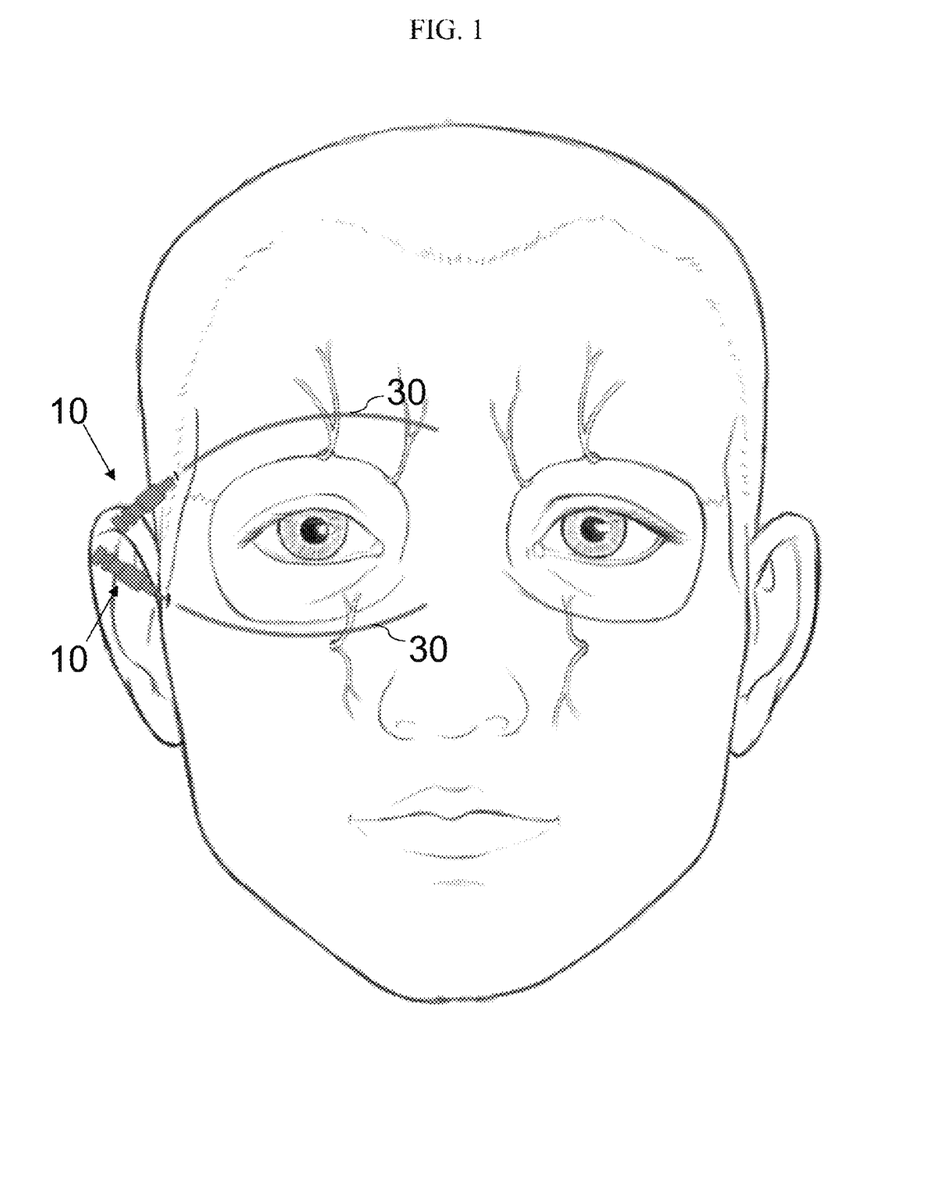
FIG. 1. Schematic illustration of an implanter for nerve stimulation according to one embodiment of the invention, illustrating a hollow needle carrying a preformed stylet.

FIG. 1 illustrates two implanters or insertion tools 10 for nerve stimulation. Although FIG. 1 illustrates the implanters 10 as being implanted for supraorbital and infraorbital nerve stimulation, in other embodiments, the implanters 10 may be used for a brain application (see FIG. 8), a spinal application (see FIG. 9), or other applications.

Figure 2:
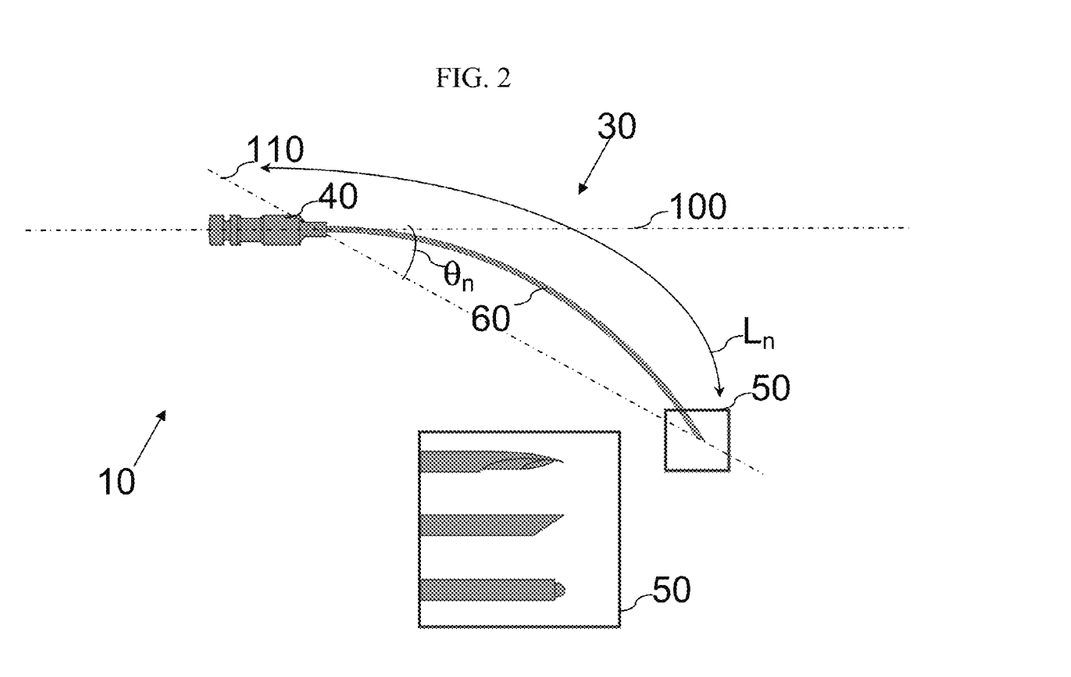
FIG. 2. Side view of the implanter of FIG. 1, illustrating three tip styles.
Figure 3:
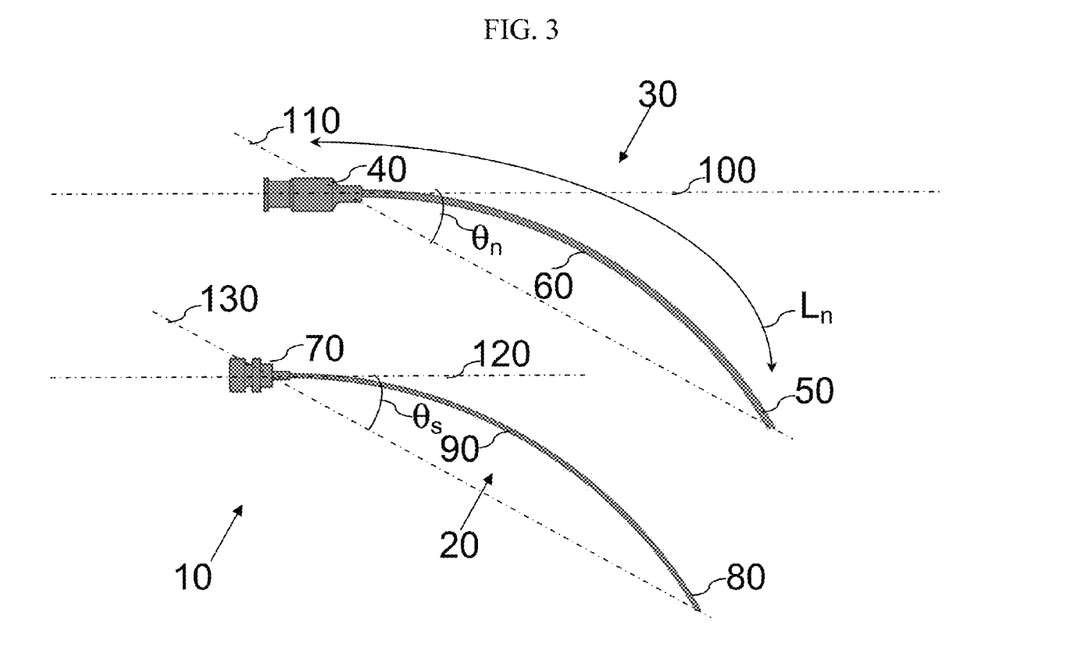
FIG. 3. Side view of the implanter of FIG. 1, illustrating the hollow needle and preformed stylet.

Referring also to FIGS. 2 and 3, each implanter 10 comprises a preformed stylet 20 and a hollow needle 30. Although FIGS. 2 and 3 illustrate a single preformed stylet 20 carried on the needle 30, as explained below, the implanter 10 comprises a plurality of preformed stylets 20 that are interchangeably insertable into a respective needle 30. The needle 30 defines a first end 40 configured to receive each preformed stylet 20, a second end 50 opposite the first end 40, and a curved portion 60 extending therebetween. Similarly, each preformed stylet 20 defines a butt end 70, a tip 80 opposite the butt end 70, and a curved portion 90 extending therebetween. The curved portion 60 of the needle 30 and the curved portion 90 of the preformed stylets 20 are of substantially congruent shapes.

In the illustrated embodiment, the first end 40 of the needle 30 defines a longitudinal axis 100. A chord line 110 drawn between the first and second ends 40, 50 defines an acute angle $\theta_n$ with respective to the longitudinal axis 100. In the illustrated embodiment, the acute angle $\theta_n$ is about 60 degrees. As explained below, however, in other embodiments, the acute angle $\theta_n$ ranges from about 20 degrees to about 80 degrees. In some embodiments, the acute angle $\theta_n$ is at least about 20 degrees, at least about 30 degrees, at least about 40 degrees, at least about 50 degrees, at least about 60 degrees, or at least about 70 degrees. In further embodiments, the acute angle $\theta_n$ is no more than 80 degrees, no more than 70 degrees, no more than 60 degrees, no more than 50 degrees, no more than 40 degrees, or no more than 30 degrees. This includes angles $\theta_n$ of about 30 degrees to about 70 degrees, or about 40 degrees to about 60 degrees. The acute angle $\theta_n$ of the needle 30 can facilitate avoiding contact with the skin surface during insertion, and thereby decrease the risk to tissue injury upon insertion.

The illustrated needle 30 defines a needle length $L_n$. In some embodiments, the needle length $L_n$ is about 50 mm to about 160 mm. In other embodiments, the needle 30 can have other lengths $L_n$. In some embodiments, the curved portion 60 of the needle 30 extends along at least half of the needle length $L_n$. In other embodiments, the curved portion 60 of the needle 30 extends along at least two-third of the needle length $L_n$. Depending on the usage requirement or other preferences for the particular implanter 10, if the curved portion 60 of the needle 30 extends along only a few millimeters near the second end 50, the needle 30 may not conform to the natural curvature of the human body.

In the illustrated embodiment, the needle 30 can be selected from the group consisting of needles 30 having a Tuohy-type or cutout second end 50 (see top of inset in FIG. 2), a slant-cut second end 50 (see middle of inset in FIG. 2), and a cylindrical or blunt second end 50 (see bottom of inset in FIG. 2). In other embodiments, the second end 50 of the needle 30 may assume any other suitable geometric form depending on the usage requirement or other preferences for the particular implanter 10, including, but not limited to, a regular polyhedral and an irregular polyhedral shape, derivatives thereof, and combinations thereof. In the illustrated embodiment, the tips 80 of the preformed stylets 20 are flush with an outer surface of the second end 50 of the needle 30 when the preformed stylet 20 is inserted into the needle 30. In other embodiments, the tip 80 of the preformed stylet 20 may be slightly recessed or protruding relative to adjacent portions of the second end 50 of the needle 30 when the preformed stylet 20 is inserted into the needle 30.

In some embodiments, the needle 30 may have an outer diameter of about 2.1 mm and an inner diameter of about 1.6 mm, corresponding to a gauge number of about 14. In other embodiments, the needle 30 may have an outer diameter of about 1.3 mm and an inner diameter of about 0.7 mm, corresponding to a gauge number of about 18. In further embodiments, the needle 30 may have dimensions corresponding to a gauge number from about 14 to about 18, wherein smaller gauge numbers indicate larger outer diameters.

The curved portions 90 of the preformed stylets 20 are of substantially congruent shapes such that the preformed stylets 20 are interchangeably insertable into the needle 30. In the illustrated embodiment, the butt end 70 of the preformed stylet 20 defines a longitudinal axis 120. When the preformed stylet 20 is carried on the needle 30, the longitudinal axis 120 of the preformed stylet 20 coincides with the longitudinal axis 100 of the needle 30. A chord line 130 drawn between the butt end 70 and the tip 80 defines an acute angle $\theta_s$ with respective to the longitudinal axis 120. The acute angle $\theta_s$ of the preformed stylet 20 is substantially the same as the acute angle $\theta_n$ of the needle 30.

Depending on the usage requirement or other preferences for the particular implanter 10, manually curving or bending the preformed stylets 20 may not achieve the desired angle $\theta_s$ and length of the curved portions 90. For example, manually bending the stylets 20 can require a high force depending on the mechanical properties of the material, and can undesirably create a sharp bend with a small bending radius. A stylet with a small bending radius can be difficult to remove once the needle 30 is positioned. Moreover, manually bending each stylet 20 may not result in the precision required for creating an interchangeable group or family of stylets 20. Thus, to create a smooth curved portion 60 substantially without sharp bends, and to create an interchangeable group of stylets 20 with requisite precision, the needle 30 are preformed or manufactured with the desired curved portion 60.

In the illustrated embodiment, the acute angle $\theta_s$ of the preformed stylet 20 is about 60 degrees. As explained below, however, in other embodiments, the acute angle $\theta_s$ ranges from about 20 degrees to about 80 degrees. In some embodiments, the acute angle $\theta_s$ is at least about 20 degrees, at least about 30 degrees, at least about 40 degrees, at least about 50 degrees, at least about 60 degrees, or at least about 70 degrees. In further embodiments, the acute angle $\theta_s$ is no more than 80 degrees, no more than 70 degrees, no more than 60 degrees, no more than 50 degrees, no more than 40 degrees, or no more than 30 degrees. This includes angles $\theta_s$ of about 30 degrees to about 70 degrees, or about 40 degrees to about 60 degrees. Like the acute angle $\theta_n$ of the needle 30, the acute angle $\theta_s$ of the preformed stylet 20 can facilitate avoiding contact with the skin surface during insertion, and thereby decrease the risk to tissue injury upon insertion.

Figure 4:
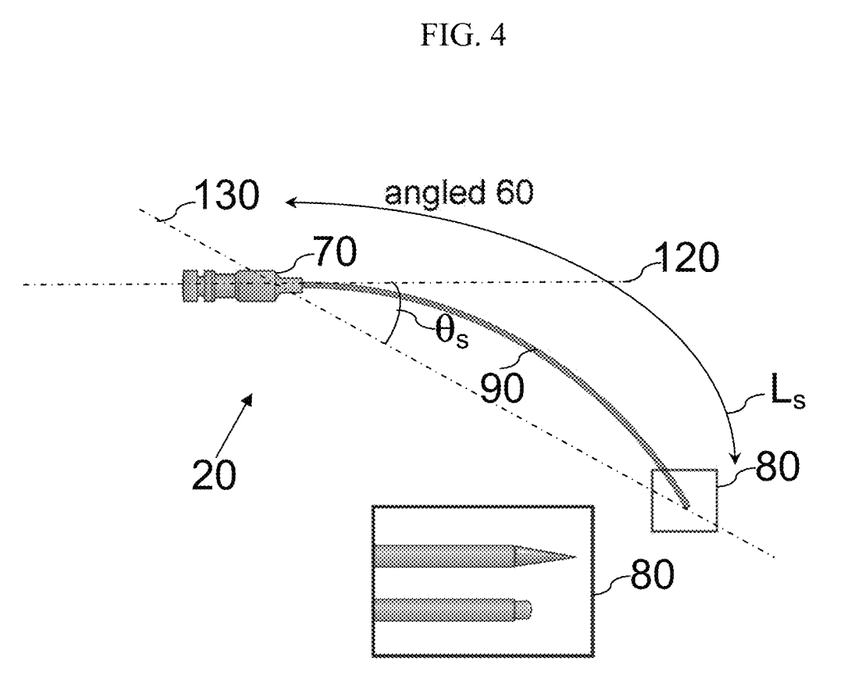
FIG. 4. Side view of the preformed stylet of FIG. 3, illustrating two tip styles.

Referring also to FIG. 4, the preformed stylets 20 can include a sharp or tapered tip 80 (see top of inset in FIG. 4) and a blunt tip 80 (see bottom of inset in FIG. 4). A sharp tip 80 may facilitate penetration of the skin and fascia during insertion of the implanter 10, while a blunt tip 80 may decrease the risk to tissue injury upon insertion of the implanter 10. In some embodiments, the tips 80 of the preformed stylets 20 may assume any other suitable geometric form depending on the usage requirement or other preferences for the particular implanter 10, including, but not limited to, a regular polyhedral and an irregular polyhedral shape, derivatives thereof, and combinations thereof.

The illustrated stylet 20 defines a stylet length $L_s$. In some embodiments, the stylet length $L_s$ is about 50 mm to about 160 mm. In other embodiments, the preformed stylet 20 can have other lengths $L_s$. In some embodiments, the curved portion 90 of each preformed stylet 20 extends along at least half of the stylet length $L_s$. In other embodiments, the curved portion 90 of each preformed stylet 20 extends along at least two-third of the stylet length $L_s$.

Figure 5:
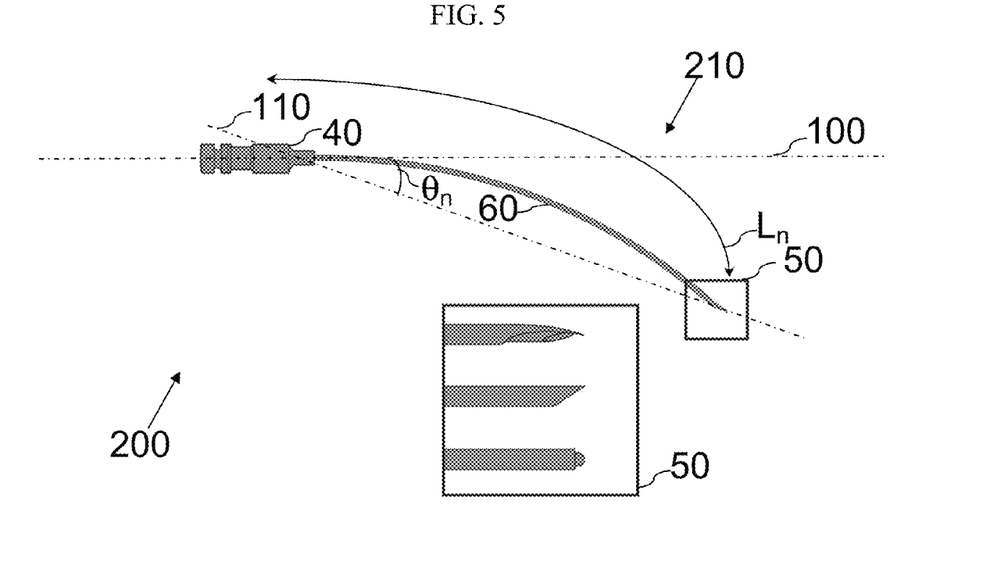
FIG. 5. Side view of an implanter according to another embodiment of the invention, illustrating a hollow needle carrying a preformed stylet.
Figure 6:
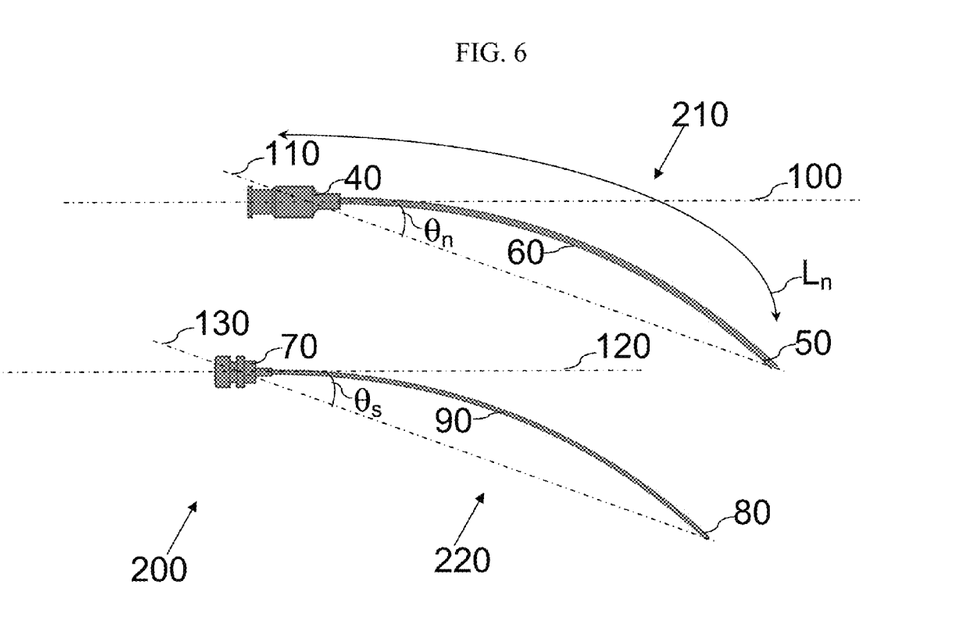
FIG. 6. Side view of the implanter of FIG. 5, illustrating the hollow needle and preformed stylet.
Figure 7:
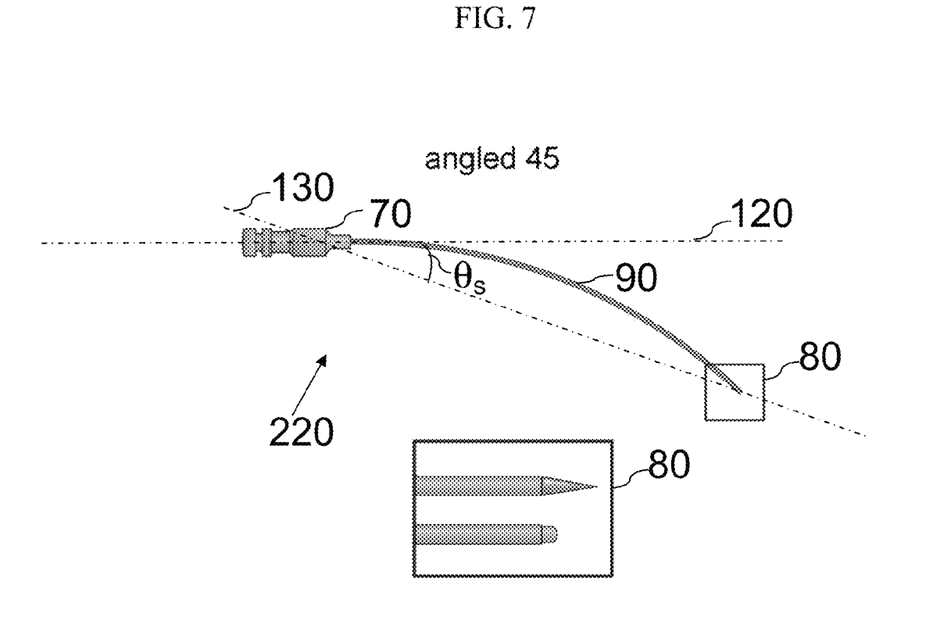
FIG. 7. Side view of the preformed stylet of FIG. 6, illustrating two tip styles.

FIGS. 5-7 illustrate the implanter 200 according to another embodiment of the invention. Structure and features of the embodiment shown in FIGS. 5-7 that correspond to structure and features of the embodiment of FIGS. 1-4 are designated hereinafter with like reference numbers. The acute angle $\theta_n$ of the needle 210 and the acute angle $\theta_n$ of the preformed stylet 220 in this embodiment are both about 45 degrees. The needle 210 curved according to this angle $\theta_n$ may be used to introduce an implant for different body part applications compared to the needle 30 having an acute angle $\theta_n$ of about 60 degrees.

3. Method of Using the Implanter

Figure 8:
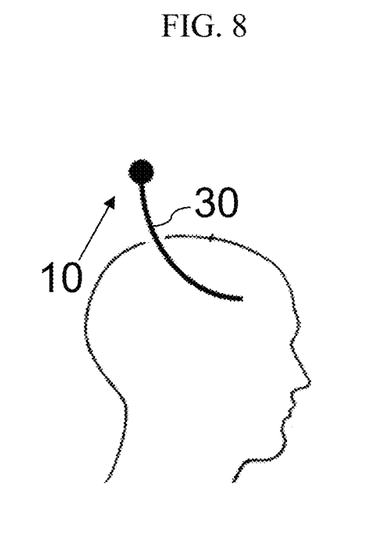
FIG. 8. Schematic illustration of the implanter of FIG. 2, illustrating an implantation within a brain.
Figure 9:
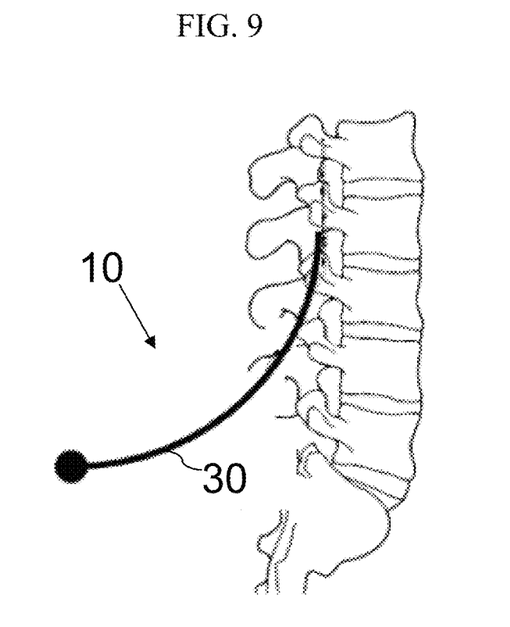
FIG. 9. Schematic illustration of the implanter of FIG. 2, illustrating an implantation within a spine.

The present disclosure is also directed to a method of introducing an implant for stimulating a nerve using the implanter 10, 200. The implants may include electrical electrodes (leads), catheters, waveguides, laser and optical fibers, and mechanical, thermal, and chemical sensors, as well as medications, radiation seeds, viral vectors, chemicals, and other suitable materials. The hollow needle 30, 210 carrying the preformed stylet 20 is inserted into a target region such as a subcutaneous region. Referring also to FIG. 8, the target region may be positioned within a brain. Referring also to FIG. 9, the target region may be positioned within a spine.

The preformed stylet 20 is withdrawn to leave the needle 30, 210 in place in the target region. In some embodiments, the needle 30, 210 carries a first preformed stylet including a first curved portion 90, and a second preformed stylet including a second curved portion 90 is inserted into the needle after the first preformed stylet 20 is withdrawn. For example, a stylet 20 with a tapered or sharp tip 80 may be inserted first into the needle 30, 210 for penetrating the skin and fascia, and then the sharp stylet 20 may be replaced with a blunt stylet 20 of the same curvature to advance the implanter 10, 200 substantially without tissue injury.

Once the stylet 20 is withdrawn from the needle 30, 210, the implant is inserted into the needle 30, 210. The needle 30, 210 is removed from the target region to expose the implant therein.

Although the invention has been described in detail with reference to certain preferred embodiments, variations and modifications exist within the scope and spirit of one or more independent aspects of the invention as described.

What is claimed is:

1. An implanter for peripheral nerve stimulation, the implanter comprising:
    a first preformed stylet having a tapered tip and a second preformed stylet having a blunt tip, each of the first and the second preformed stylets including a butt end that defines a longitudinal axis, its respective tip opposite the butt end, and a curved portion extending therebetween, each of the first and the second preformed stylets defining a stylet length, and the curved portion of each of the first and the second preformed stylets extending along the entire stylet length; and
    a hollow needle including a first end, a second end opposite the first end, and a curved portion extending therebetween, the needle being configured to receive each of the first and the second preformed stylets, the needle defining a needle length, and the curved portion of the needle extending along the entire needle length;
    wherein a chord line drawn between the butt end and the tip defines an acute angle with respect to the longitudinal axis, the acute angle being about 60 degrees such that each of the first and the second preformed stylets conforms to the natural curvature of a human body for supraorbital or intraorbital nerve stimulation; and
    wherein the curved portion of the needle and the curved portion each of the first and the second preformed stylets are of substantially congruent shapes such that the first and the second preformed stylets are interchangeably insertable into the needle, the first preformed stylet being insertable first into the needle such that the tapered tip penetrates skin and facia and the second preformed stylet being insertable second into the needle such that the blunt tip advances the needle to a target region.

2. The implanter of claim 1, wherein the needle is selected from the group consisting of needles having a slant-cut second end, a cylindrical second end, and a cutout second end.

3. The implanter of claim 1, wherein at least one of the tips of the preformed stylets is flush with an outer surface of the second end of the hollow needle when the preformed stylet is inserted into the needle.

4. A method of introducing an implant for stimulating a peripheral nerve, the method comprising:
    inserting a first preformed stylet at least partially into a hollow needle, the first preformed stylet including a butt end that defines a first longitudinal axis, a tapered tip opposite the butt end, and a curved portion extending therebetween, the first preformed stylet defining a first stylet length, and the curved portion of the first preformed stylet extending along the entire first stylet length, the needle including a first end, a second end opposite the first end, and a curved portion extending therebetween, the needle defining a needle length, and the curved portion of the needle extending along the entire needle length, the curved portion of the needle and the curved portion of the first preformed stylet being of substantially congruent shapes;
    inserting the needle and the first preformed stylet such that the tapered tip of the first preformed stylet penetrates skin and fascia;
    withdrawing the first preformed stylet from the needle while leaving the needle in place;
    inserting a second preformed stylet at least partially into the needle, the second preformed stylet including a butt end that defines a second longitudinal axis, a blunt tip opposite the butt end, and a curved portion extending therebetween, the second preformed stylet defining a second stylet length, and the curved portion of the second preformed stylet extending along the entire second stylet length, the curved portion of the needle and the curved portion of the second preformed stylet being of substantially congruent shapes;
    advancing the blunt tip of the second stylet such that the needle is guided to a target region;
    withdrawing the second preformed stylet to leave the needle in place in the target region;
    inserting the implant into the needle; and
    removing the needle from the target region to expose the implant therein;

wherein a first chord line drawn between the butt end and the tip of the first preformed stylet defines a first acute angle with respect to the first longitudinal axis and a second chord line drawn between the butt end and the tip of the second preformed stylet defines a second acute angle with respect to the second longitudinal axis, each of the first and the second acute angles being at least 20 degrees such that each of the plurality of preformed stylets conforms to the natural curvature of a human body for supraorbital or intraorbital nerve stimulation.

5. The method of claim 4, wherein the target region is positioned within a brain.

6. The method of claim 4, wherein the target region is positioned within a spine.

7. The method of claim 4, wherein the hollow needle is selected from the group consisting of hollow needles having a slant-cut second end, a cylindrical second end, and a cutout second end.

8. The method of claim 4, wherein the first end defines a longitudinal axis, and wherein a chord line drawn between the first and second ends defines an acute angle with respective to the longitudinal axis.

9. A method of introducing an implant for stimulating a peripheral nerve, the method comprising:
  inserting a first preformed stylet at least partially into a first hollow needle to create a first implanter combination, the first preformed stylet including a butt end, a tapered tip opposite the butt end, and a curved portion extending therebetween, wherein the tip of the first preformed stylet is a first type;
  penetrating, by the first implanter combination, skin and fascia and advancing the first implanter combination a first distance; withdrawing the first preformed stylet from the first hollow needle and leaving the needle in place;
  inserting a second preformed stylet at least partially into the first hollow needle to create a second implanter combination, the second preformed stylet including a butt end, a blunt tip opposite the butt end, and a curved portion extending therebetween, wherein the tip of the second preformed stylet is a second type different than the first type;
  advancing the second implanter combination a second distance beyond the first distance such that the second preformed stylet guides the needle to a target region; and
  withdrawing the second preformed stylet from the first hollow needle.

10. The method of introducing an implant for stimulating a peripheral nerve of claim 9, wherein the first preformed stylet, the second preformed stylet, and the needle are substantially congruent in shape.

11. The method of introducing an implant for stimulating a peripheral nerve of claim 9, further comprising:
  inserting an implant into the first needle; and
  removing the needle from the target region to expose the implant therein.

* * * * *